Figure 4:
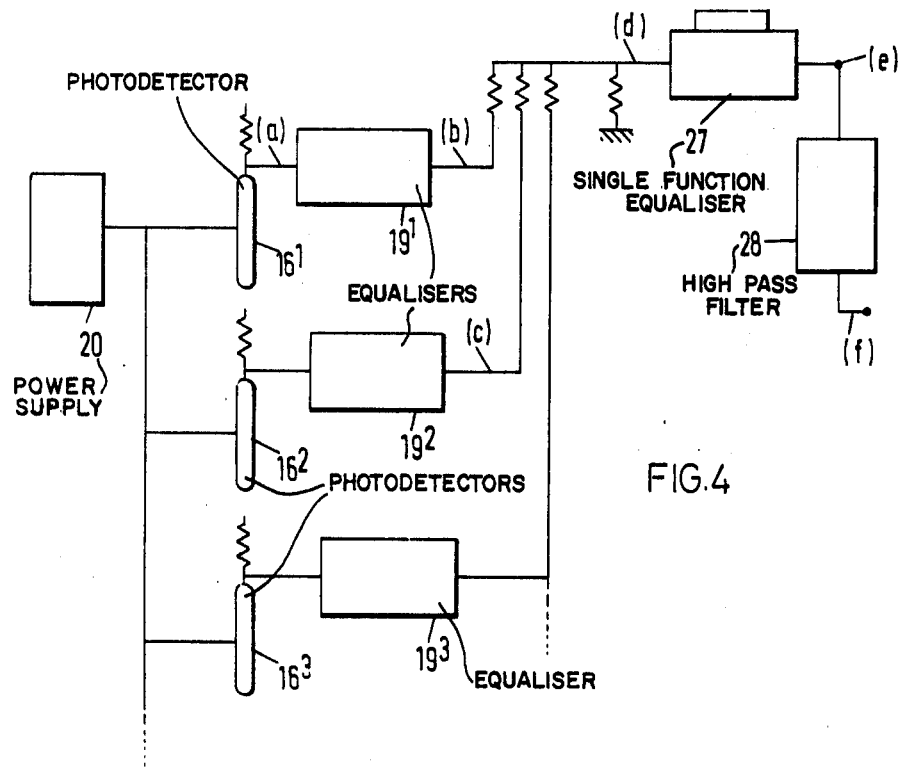

United States Patent [19] [11] 4,048,510
Clarke et al. [45] Sept. 13, 1977

[54] CIRCUIT ARRANGEMENTS FOR CONTROLLING DETECTOR SIGNALS IN SURFACE INSPECTION SYSTEMS

[75] Inventors: Graham Morley Clarke; George Fisher, both of Edinburgh, Scotland

[73] Assignee: Ferranti Limited, Hollinwood, England

[21] Appl. No.: 660,928

[22] Filed: Feb. 24, 1976

[30] Foreign Application Priority Data

Feb. 27, 1975 United Kingdom ............ 8168/75
Mar. 27, 1975 United Kingdom .......... 13109/75

[51] Int. Cl.² .................................. G01N 21/32
[52] U.S. Cl. .......................... 250/563; 250/214 AG; 356/200
[58] Field of Search ............ 250/562, 563, 571, 572, 250/214 AG, 559; 356/199, 200, 237, 239

[56] References Cited

U.S. PATENT DOCUMENTS

| 3,582,661 | 6/1971 | Emmasingel | 250/562 |
| 3,584,963 | 6/1971 | Wisner | 356/237 |
| 3,601,615 | 8/1971 | Maeda | 250/562 |
| 3,843,890 | 10/1974 | Anthony et al. | 250/572 |

Primary Examiner—David C. Nelms
Attorney, Agent, or Firm—Cameron, Kerkam, Sutton, Stowell & Stowell

[57] ABSTRACT

In a surface inspection system a detector responds to light received from the surface to give a detector signal including disturbances due to surface faults, and includes an equalizer circuit to control the gain of a photomultiplier, and therefore signal amplitude, in response to a peak level detector, to control the level of the signal in relation to the amplitude of the disturbances and a band-pass filter to compensate for variations in the signals due to changes in the optical gain of the detector. The equalizer circuit is an amplifier and the control is achieved by way of feedback and feedforward control loops. In a modification the system may comprise a row of detectors and the equalizer circuit may be arranged to accommodate changes in the amount of light received at the junctions of detectors.

10 Claims, 11 Drawing Figures

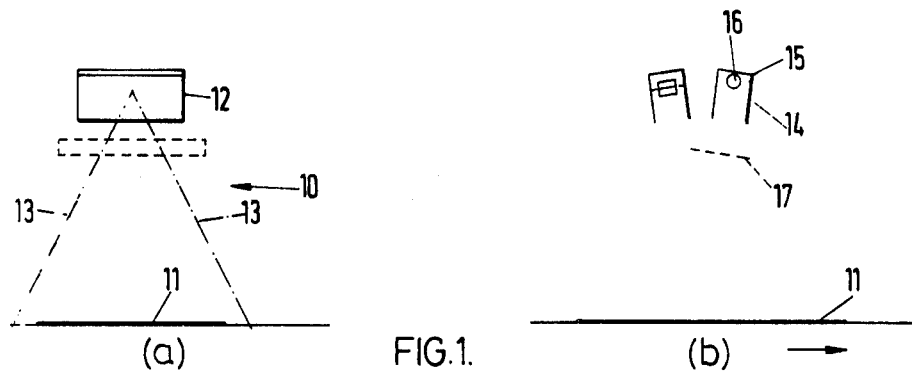
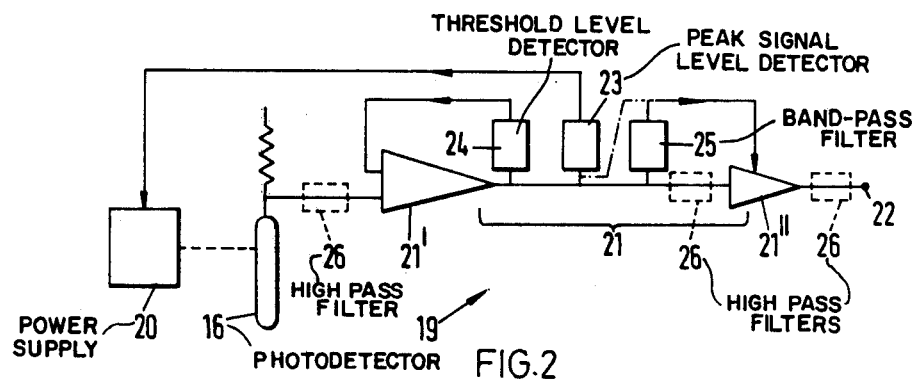
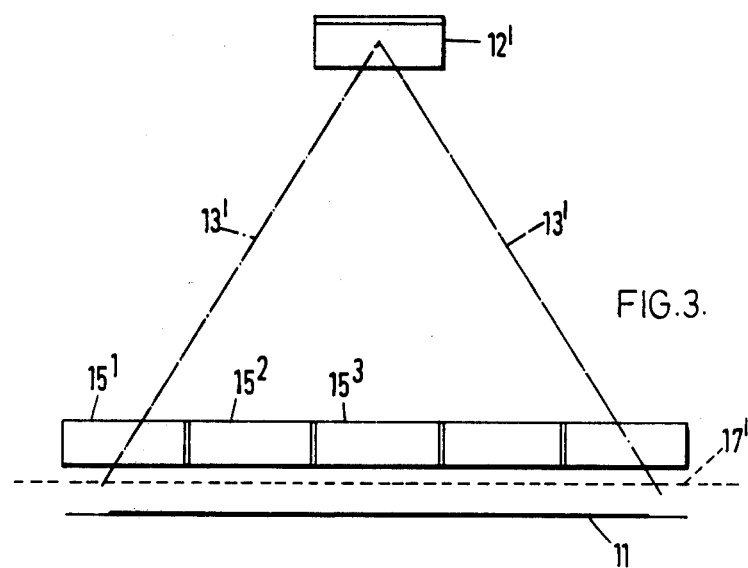

CIRCUIT ARRANGEMENTS FOR CONTROLLING DETECTOR SIGNALS IN SURFACE INSPECTION SYSTEMS

This invention relates to the detection of faults in surfaces and in particular to circuit arrangements associated with such detection.

Surface inspection systems are widely used in relation to moving strip-like surfaces such as those of paper webs, plastics material and metals. One type of inspection system with which this invention is concerned comprises a source of a beam of optical radiation, means to scan the beam repetitively across the surface transversely to the direction of motion of the surface and a detector to collect optical radiation emanating from the surface and to produce a fault signal in response to a change in the radiation collected.

The terms "optical radiation" and "light", are used in this specification to refer to electromagnetic radiation in the infra-red, visible and ultra-violet parts of the spectrum.

The detector produces an electrical signal during each scan of the surface, which signal has a mean level, due to the general background level of light emanating from the surface in the absence of a fault and ambient light, superimposed upon which are disturbances due to surface faults and variations due to changes in optical gain of the detection means throughout the scan.

In use with a particularly wide web it may be necessary to employ a plurality of detectors positioned adjacent each other ocross the width of the web. Each detector produces an electrical signal of the above described nature during a separate portion of each scan but the overall signal for the scan is complicated by the junctions between adjacent detectors.

It will be appreciated that in subsequent circuitry used to process the parts of the signal due to faults, that is, the disturbances for example, to count them, it is necessary to separate these disturbances, from the remainder of the signal.

According to the present invention a surface inspection system includes a detector having photodetection means responsive to light received to produce a detector signal having an amplitude related to the intensity of the light received, and an equalisation circuit arrangement comprising amplifier means operable to amplify the detector signal, first signal level detection means responsive to signals of the amplifier means to control the level of the detector signal applied to the amplifier means, second signal level detection means responsive to signals of the amplifier means to compensate for components of the detector signal due to the reception of ambient light, and band-pass filter means responsive to the signals of the amplifier means to compensate for variations in the signals, due to changes in the optical gain of the detector, by varying the gain of the amplifier means in accordance with said variations.

Preferred embodiments of such an equalisation circuit arrangement in effect provide separate feedback and feedforward controls for the overall signal output.

For a surface inspection system employing a plurality of adjacent detectors there may be provided further equalisation means operable to remove from the composite output signal variations due to the combination of the output signals of adjacent detectors. The further equalisation means may comprise a further amplification means and further filter means operable to control the gain of the said further amplifier means to eliminate variations in amplitude of the output signal.

The first signal detecting means may comprise a peak level detector for controlling signal levels produced by the photodetection means in relation to a peak level by applying a feedback signal to control the operating level of the photodetection means. The second signal level detecting means may comprise thresholding means operative to remove said ambient light components by providing a threshold signal to the amplifier means in combination with the detector signal.

The amplifier means may comprise two serially connected amplifiers and the band-pass filter means may then comprise a band-pass filter network responsive to signals of the first amplifier to control the gain of the second amplifier or may comprise a high pass filter network through which the signal passes to the second amplifier and a low pass filter responsive to signals of the first amplifier to control the gain of the second amplifier.

Embodiments of the invention will now be described by way of example with reference to the accompanying drawings, in which:

FIGS. 1(a) and 1(b) show front and side views respectively of surface inspection apparatus employing a single detector, FIG. 2 is a block diagram of an equalisation circuit arrangement according to the present invention, FIG. 3 shows a front view of surface inspection apparatus employing a plurality of detectors.

FIG. 4 is a block diagram of a modified equalisation circuit arrangement including further equalisation means used with the detectors of the inspection apparatus of FIG. 3, FIGS. 5(a) to (f) show waveforms of signals appearing at like lettered points in the circuit arrangement of FIG. 4.

Referring to FIGS. 1(a) and 1(b) surface inspection apparatus comprises a scanning station 10, located above a surface 11, the scanning station comprising a housing 12 containing a light source, conveniently a laser, an optical arrangement to focus the laser beam onto the surface, and a rotatable multifaceted mirror to scan the beam repetitively over the surface, transversely to the direction of motion of the surface, between the scan limits indicated by chain lines 13. Light reflected from the surface is collected in a detector 14 comprising an enclosure housing 15 containing a photodetector 16, conveniently a photomultiplier tube, which produces a detector signal having an amplitude related to the intensity of light incident upon it. The detector is intended to operate with diffuse light and the enclosure has reflecting internal walls by which diffuse light entering the enclosure is directed to the photodetector, the intensity of the light incident upon the detector being related to the amount of light entering the enclosure. If the surface being scanned is primarily diffusely reflecting then the light collected is in a diffuse form as it enters the detector enclosure; if the surface is primarily specularly reflecting then in order to obtain an even distribution of light a diffuser 17 of translucent material is placed between the surface and the detector. In operation the boundaries of the scanning beam are chosen such that each scan begins before the beam engages the surface and terminates after the beam has left the surface. Thus for a single scan, the detector signal comprises a back-ground "black" level signal due to the scanning of a non-reflective background and ambient light entering the detector, followed by an increase in signal in the form of a pedestal during the time that the beam crosses the surface and receives reflected light, followed by a return to the "black" level. The pedestal part of the signal contains a component due to ambient light, possible variations in level due to variations in optical gain of the detector throughout the scan, and disturbances due to blemishes at the web surface changing its reflection characteristics.

Referring to FIG. 2 which shows a block diagram of an equaliser circuit arrangement 19 the photodetector 16 is shown as a photomultiplier receiving power from a power supply 20. The output signal from the photomultiplier, the detector signal, is applied to one input terminal of a first amplifier 21' of amplifier means 21. The output terminal of the amplifier 21' is connected by way of a second amplifier 21" to a circuit output terminal 22. Connected to the output terminal of the amplifier 21', to be controlled by its output signal, is first signal level detection means comprising a peak signal level detector 23. This determines the peak level reached by the pedestal during a scan and for the subsequent scan controls the sensitivity of the photodetector. Changes in the detector signal level due, for instance, to absorbent faults produce high frequency disturbance pulses extending from the pedestal towards the "black" level; the sensitivity of the photodetector is controlled in the following scan to provide a predetermined maximum signal level in respect of fault disturbances irrespective of the intensity of the signal returned from the material. In the case of a photomultiplier photodector shown this control of sensitivity is achieved through control of the power supply 20.

Also connected to the output terminal of the amplifier 21' is a second signal level detection means 24 comprising a threshold level detector which responds to a mean level of output signal at the "black" level, that is, when the beam is not in engagement with the surface, to provide an offset signal to a second input terminal to the amplifier 21' to remove the effects of stray ambient light and system noise from the amplified output signal.

Further connected to the output terminal of the amplifier 21' is a filter means 25 comprising a band-pass filter. This is arranged to block high frequency disturbances due to surface faults and low frequency variations associated with change in level over the scan upon which the peak detector 23 operates, but to pass variations in the output signal of an intermediate frequency. Variations of the signal due to variations in optical gain of the system occur at the intermediate frequency and the filtered signal produced by the filter 25 is used to control the gain of the amplifier 21" such that the circuit output signal at the terminal 22 comprises a flattened pedestal in the absence of the above discussed fault and low frequency variations.

In the circuit as so far described a typical signal produced at the terminal 22 comprises a flattened pedestal signal on a zero, or near-zero, level background level and having superimposed thereon disturbances due to surface faults, which disturbances are scaled to a predetermined maximum amplitude. To eliminate any d.c. components of the output signal, for example, the pedestal or a non-zero background level, a high pass filter 26, which may be a simple resistor-capacitor combination, may be included in the circuit; it may be located at one or more of the locations shown by a ghosted block, that is, at the output terminal 22, before the amplifier 21" or before the amplifier 21' at the input to the equaliser circuit.

It will be appreciated that if a high pass filter network 26 is employed at or before the input to the second amplifier 21" then the filter network 25 may comprise a simple resistor-capacitor 'low'-pass network to block the disturbance signals but pass system optical gain variations, low frequency variations due to level changes between scans being removed by the feedback loop including the level detector 23. If desired the feedback loop may be isolated further from disturbance signals by connecting the level detector 23 to the output of filter 25, as shown in chain lines, instead of directly to the output of amplifier 21'.

FIG. 3 shows a side view of an alternative form of surface inspection system for use with wide webs. It will be appreciated that by employing a high intensity well-defined beam provided by a laser that the beam can be brought to a focus at the surface from a scanning station whose height above the surface is directly proportional to the surface width. However, the intensity of the reflected light decreases in proportion to the square of the distance so that it becomes impracticable merely to increase the separation between the surface and the detector. The system shown in FIG. 3 combines the advantages of both methods in that a single scanning station is employed at a suitable distance above the surface in combination with a plurality of detectors $15^1$, $15^2$, ... placed closer to the surface and stacked adjacent each other to provide reflected light reception for the whole width of the web. A diffuser 17' is employed when the reflection characteristics of the web are primarily specular.

The photomultiplier detection means of each detector has its gain set by means of its power supply such that the output signals of adjacent detectors are equalised and equal signals provided for equal light inputs. The outputs of the individual photomultipliers are combined in a summing amplifier before being fed to an equaliser circuit of FIG. 2.

Alternatively each detector may be fitted with an equaliser circuit and the circuit output signals combined to provide a system output signal for the whole scan and FIG. 4 is a block diagram of a combining circuit arrangement in which it is shown how the output signals of the individual detectors are combined to provide a system output signal. In either case with multiple detectors the reception of reflected light is complicated by the effects of junctions between adjacent detectors at which junctions are received reflected light from portions of the surface and for which detector might be expected not to occur.

Figure 5:
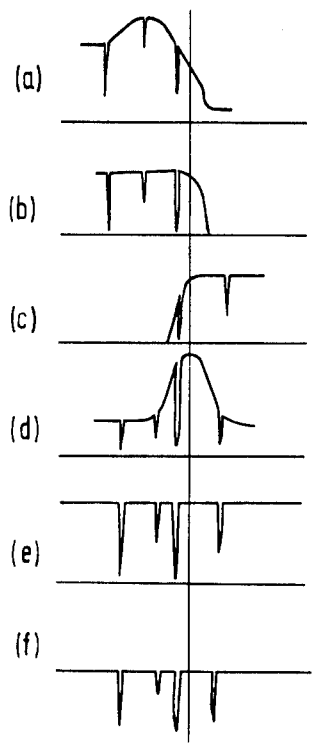

The manner in which the equaliser circuit of the present invention is used to eliminate the effects of the junction will be seen with reference to the combining circuit arrangement of FIG. 4, and FIG. 5 which shows the waveforms of signals appearing at points in the combining circuit. The final part of a detector signal (a) from the first detector 16' decays as the main part of the reflected light moves between the two detectors $16^1$ and $16^2$ due to the diffused nature of the light reaching the detectors; the increase in detector output signal as the diffused light begins to reach the second detector $16^2$ is correspondingly slow. The equalising circuits $19^1$, $19^2$... associated with the respective detectors produce well defined pedestal signals (b) and (c), if no d.c. blocking is employed, which, it will be seen, overlap in time. Thus as the output signals of the detector equalisers are combined at (d) there is a temporary increase in pedestal amplitude as the signals are added. The combined signals are passed through further equalisation means comprising a single function equaliser 27 comprising an amplifier and gain controlling band-pass filter similar to components 21 and 25 in FIG. 2. The system output signal (e) appearing at the output of the equaliser 27 comprises a pedestal signal extending for the whole of the scan period in which the beam is in engagement with the web, from which pedestal variations due to differences between, and changes in, the optical characteristics of the detectors have been removed and in having superimposed thereon variations due to the detection of surface faults, whose amplitudes have been equalised to provide a predetermined maximum-level by each equaliser. If desired, the d.c. component of the pedestal may be removed by means of a high pass filter 28 which by blocking d.c. levels produces a system output signal (f) comprising only disturbances due to detected faults. If the equalisers $19^1$, $19^2$, . . . contain means to block d.c. signals the filter 28 may not be required.

It will be appreciated that the above described arrangement relating to a plurality of detectors may be employed with an inspection system comprising a plurality of the scanning station and detector unit arrangements shown in FIG. 1, the units being spaced across the surface such that the reception boundaries of adjacent detectors meet or overlap. With the form of combining circuits in which photomultiplier outputs are summed and passed through a single equaliser circuit the peaks appearing at the junctions are eliminated in the equaliser circuit.

In the case of translucent material the diffuser 17 is not essential in respect of absorptive faults but is necessary in respect of the detection of holes through the web which permit direct transmission of the directional beam. Similarly in order to detect adequately holes in opaque material the diffuser is required.

In embodiments of the inspection system described with reference to FIG. 3 wherein a diffuser 17' is interposed between the surface and the detectors, a primary function of the diffuser is to remove directional chracteristics of the light in the direction of scan to avoid light loss at the junction of adjacent detectors.

The diffuser may be isotropic in that the light is totally diffused in all directions or it may have directional properties such that light is only diffused in the direction of scan to eliminate light loss at the said junctions.

Such an anisotropic diffuser may comprise a sheet of transparent material having a series of closely spaced ridges, extending in the direction of travel of the surface, ruled or impressed on one surface thereof in the manner of diffraction grating lines. Light transmitted by the diffuser retains any polar optical response characteristics of the surface being inspected in the direction of travel of the surface and may be used in surface analysis procedures.

In general the detectors, and particularly the openings to the light collecting enclosures, extend transversely to the direction of motion of the surface. Where desired, or where the nature of the inspected surface dictates, the longer openings to the light collecting enclosures may extend at some angle other than 90° to the direction of travel of the surface; the diffuser is then similarly orientated such that the ridges extend in a direction transversely to the longer openings of the light collecting enclosures. An anisotropic diffuser as described may be employed with a single light collecting enclosure in the embodiment shown in FIG. 1 when it is desired to obtain information as to the polar optical response of the surface generally in the direction of travel of the surface.

In the foregoing description operation of the equaliser circuit arrangement has been described with reference to fault disturbances of the detector signal of a single polarity, that is, all negative-going disturbances. It will be appreciated that he circuit can easily be arranged to process disturbances of the polarity or both polarities.

What we claim is:

1. A surface inspection system including a detector having photodetection means responsive to light received to produce a detector signal having an amplitude related to the intensity of the light received, and an equalisation circuit arrangement comprising amplification means operable to amplify the detector signal, first signal level detector means responsive to an amplified detector signal appearing in the amplification means to control the level of the detector signal applied to the amplification means, second signal level detection means responsive to said amplified detector signal to compensate for components of the detector signal due to the reception of ambient light, and band-pass filter means responsive to said amplified detector signal to compensate for variations in said signal due to changes in the optical gain of the detector by controlling the gain of the amplification means in accordance with said variations.

2. A surface inspection system as claimed in claim 1 in which the first signal level detection means of the equalisation circuit arrangement comprises a peak signal level detector of the amplified detector signal, inclusive of high frequency disturbances, in each scan, the detector being operable to provide a feedback signal to the photodetection means to control the sensitivity thereof in the next scan to receive light in such a sense that the photodetector signal is reduced if the peak signal level of the amplified signal increases, and vice versa.

3. A surface inspection system as claimed in claim 1 in which the second signal level detection means of the equalisation circuit arrangement comprises thresholding means operable to remove said ambient light components of the signal by providing s threshold signal by way of a feedback path to the input of the amplification means to offset said ambient light components of the detector signal.

4. A surface inspection system as claimed in claim 1 in which the amplification means comprises two amplifiers and in which the band-pass filter means is responsive to signals of the first amplifier to control the gain of the second amplifier.

5. A surface inspection system as claimed in claim 4 in which the band-pass filter means comprises a high-pass filter network, operable to pass fault signal disturbances, in series with the input to the second amplifier and a low-pass filter, operable to block said fault signal, arranged to receive the output of the first amplifier and to control the gain of the second amplifier.

6. A surface inspection system as claimed in claim 1 including high-pass filter means at the output of the amplifier means to remove d.c. components of the signal.

7. A surface inspection system as claimed in claim 1 including high-pass filter means at the input to the amplifier means to remove d.c. components of the detector signal.

8. A surface inspection system including a plurality of adjacent detectors each having photodetection means responsive to light received from a different part of the surface to produce a detector signal having an amplitude related to the intensity of the light received, summing means operable to combine the individual detector signals, and an equalisation circuit arrangement adapted to receive a signal from the summing means comprising amplification means operable to amplify the detector signals, first signal level detection means responsive to an amplified detector signal appearing in the amplification means to control the level of the detector signal applied to the amplification means, second signal level detection means responsive to said amplified detector signal to compensate for components of the detector signal due to the reception of ambient light, and band-pass filter means responsive to said amplified detector signal to compensate for variations in said signal due to changes in the optical gain of the detector by controlling the gain of the amplification means in accordance with said variations.

9. A surface inspection system including a plurality of adjacent detectors each having photodetection means and responsive to light received from a different part of the surface to produce a detector signal having an amplitude related to the intensity of the light received, each detector having associated therewith an equalisation circuit arrangement comprising amplification means operable to amplify the associated detector signal, first signal level detection means responsive to an amplified detector signal appearing in the amplification means to control the level of the detector signal applied to the amplification means, second signal level detection means responsive to said amplified detector signal to compensate for components of the detector signal due to the reception of ambient light, and band-pass filter means responsive to said amplified detector signal to compensate for variations in said signal due to changes in the optical gain of the detector by controlling the gain of the amplification means in accordance with said variations, said equalisation circuit arrangements providing a composite output signal at a circuit node to which each equalisation circuit output is connected, and filter means connected to receive signals from said signal node and operable to pass signal variations at high frequencies due to disturbances and to block signal variations at low frequencies due to the combination of output signals of adjacent detectors.

10. A surface inspection system including a plurality of adjacent detectors each having photodetection means and responsive to light received from a different part of the surface to produce a detector signal having an amplitude related to the intensity of the light received, at least one equalisation circuit arrangement comprising amplification means operable to amplify the composition, or an individual detector, signal, first signal level detection means responsive to an amplified detector signal appearing in the amplification means to control the level of the detector signal applied to the amplification means, second signal level detection means responsive to said amplified detector signal to compensate for components of the detector signal due to the reception of ambient light, and band-pass filter means responsive to said amplified detector signal to compensate for variations in said signal due to changes in the optical gain of the detector by controlling the gain of the amplification means in accordance with said variations, and light diffusing means, through which light from the surface reaches each detector, having anisoptropic diffusing properties arranged to diffuse the light only in the direction of a line connecting adjacent detectors so as to cause light which would otherwise be incident upon the junction between adjacent detectors to be diffused and be incident upon either detector or both detectors.

* * * * *

UNITED STATES PATENT AND TRADEMARK OFFICE
CERTIFICATE OF CORRECTION

PATENT NO. : 4,048,510

DATED : Sept. 13, 1977

INVENTOR(S) : Graham Morley Clarke et al.

It is certified that error appears in the above-identified patent and that said Letters Patent are hereby corrected as shown below:

Column 6, line 46, "s" should read --a--;

column 8, line 10, "low" should read --lower--;

column 8, line 19, "composition" should read --composite--.

Signed and Sealed this

Twenty-first Day of February 1978

[SEAL]

Attest:

RUTH C. MASON
Attesting Officer

LUTRELLE F. PARKER
Acting Commissioner of Patents and Trademarks